United States Patent [19]

Schroeder et al.

[11] 4,396,579

[45] Aug. 2, 1983

[54] LUMINESCENCE DETECTION DEVICE

[75] Inventors: Hartmut R. Schroeder, Elkhart; Paul O. Vogelhut, Mishawaka, both of Ind.

[73] Assignee: Miles Laboratories, Inc., Elkhart, Ind.

[21] Appl. No.: 290,656

[22] Filed: Aug. 6, 1981

[51] Int. Cl.³ ............... C12M 1/20; G01N 21/76; B01L 3/0
[52] U.S. Cl. .................. 422/52; 422/61; 422/68; 422/102; 435/291; 435/835; 436/135; 436/172; 436/546
[58] Field of Search ............ 422/52, 61, 68, 102, 422/104, 66; 23/230 R, 230 B; 435/8, 35, 291; 436/135, 172, 546

[56] References Cited

U.S. PATENT DOCUMENTS

| | | | |
|---|---|---|---|
| 3,923,462 | 12/1975 | Cavanagh | 422/52 X |
| 4,099,920 | 7/1978 | Heiss | 422/52 |
| 4,154,795 | 5/1979 | Thorne | 422/102 |
| 4,231,754 | 11/1980 | Vogelhut | 23/230 B |
| 4,294,931 | 10/1981 | Levin et al. | 422/61 |

OTHER PUBLICATIONS

Seitz, W. R. et al., Anal. Chem. 46:188-202, pp. 191-192.

*Primary Examiner*—Michael S. Marcus
*Attorney, Agent, or Firm*—Roger N. Coe

[57] ABSTRACT

A luminescence detection device for quantitatively detecting an analyte in a liquid sample, which device comprises (1) a reaction compartment having, along a primary axis, opposite end portions, a first of which is for introduction of fluid reagents and sample into the compartment and the other of which forms a light transmissive aperture of predetermined size, the compartment being suitable to hold a composition which luminesces in response to contact with analyte-containing sample; (2) closure means in said first end portion for admitting a cannula, whereby fluid is introduced into said compartment, and for closing the reaction compartment; (3) a photoresponsive imaging layer; (4) means for associating the photoresponsive imaging layer and the reaction compartment such that the photoresponsive imaging layer is positioned preferably substantially perpendicular to the primary axis of the reaction compartment, at a predetermined distance from the end portion forming the aperture so as to be exposed to light emanating therefrom; and (5) means for preventing exposure of the photoresponsive imaging layer to ambient light.

10 Claims, 7 Drawing Figures

LUMINESCENCE DETECTION DEVICE

BACKGROUND OF THE INVENTION

1. Field of the Invention

The present invention relates generally to the field of analytical devices and, more particularly, to those used for the quantitative luminescent assay of an analyte in a sample.

2. Description of the Prior Art

The prior art has developed a wide variety of test compositions and methods for the determination of specific constituents in liquids such as urine and blood. Such prior art test systems have conventionally been of the type which include in the reagent composition one or more chromogenic redox indicators which are either directly responsive to the analyte to be determined or are combined with and react to the product of an analyte responsive system. The extreme sensitivity of luminescence assays and their applicability to the important analytical intermediates ATP, NAD(H), and peroxide have led to the exploitation of both chemiluminescence and bioluminescence as analytical tools in clinical chemistry. An excellent review of analytical luminescence is that by Whitehead et al., Clin. Chem., 25:1531-1546 (1979).

Until recently, most luminescence measurements have been made by using individually constructed apparatus or commercial equipment modified to meet the peculiar requirements of luminescence. Commercially available instruments which have been modified include photometers, fluorometers and scintillation counters. (see Whitehead, supra).

Another approach which has been taken in efforts to measure luminescence is the exposure of photographic film to light emitted by the luminescent reaction. Chemiluminescent reactions have been monitored on film by others to detect enhancers, inhibitors, catalysts and oxidants in various systems. Isacsson et al, Analytica Chim. Acta 68:339 (1974); Babko et al., J. Anal. Chem. U.S.S.R., 20:1150 (1965); Lukovskaya et al., J. Anal. Chem. U.S.S.R., 26:1492 (1971); Babko et al., Zavod. Lab. 29:404 (1963); and Babko et al., Ukri Khim. Zh. 29:57 (1963). However, none describe any instrument.

Another suggestion was to inject a sample and chemiluminescent reagents into a sealed container surrounded by photographic film and measuring the film exposure as a function of concentration. [Seitz, W. R. et al. Anal. Chem., 46:188-202, at 191-192 (1974)].

Vogelhut, U.S. Pat. No. 4,231,754, assigned to the present assignee, discloses a test device for determining an analyte in a sample comprising unitary solid carrier means incorporated with a first reagent system responsive to the presence of said analyte to produce a reaction product and a second reagent system responsive to the presence of said reaction product to produce luminescence. The test device can further comprise a photoresponsive layer physically associated with said carrier means and responsive to light produced by the chemiluminescent system.

Cavanaugh, U.S. Pat. No. 3,923,462, discloses an automated apparatus for the detection of ozone or pollutants in ambient air. A sample of air is passed through a light tight enclosure to react with a material which luminesces in the presence of ozone, such as Rhodamine B, or with a material which normally luminesces (such as in black light) and is quenched in the presence of ozone. Photographic film in the enclosure is spaced apart from and exposed to the chemiluminescent system. The grain density of the film is increased by exposure to the luminescent reaction. Denser film indicates more pollutant present. However, reliance on grain density requires either sophisticated instrumentation or estimation between small shades of color difference.

SUMMARY OF THE INVENTION

Figure 1:
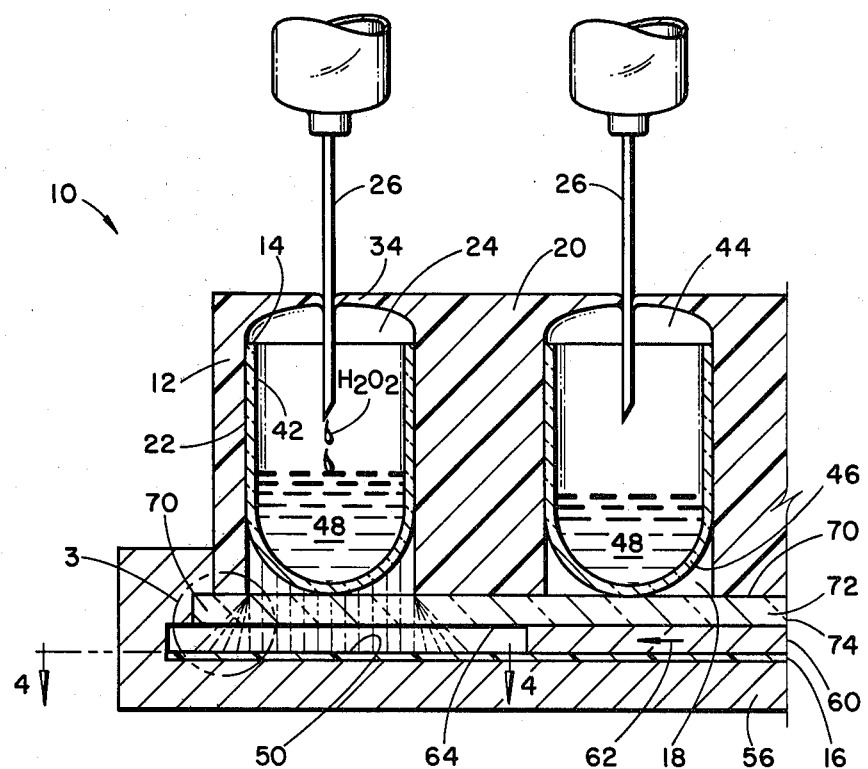
FIG. 1 is a partial, cross-sectional plan view of one preferred embodiment of the luminescence detection device of the invention.

The luminescence detection device of the present invention employs simple, inexpensive components and allows convenient quantitative visual read out of luminescence for detection of reaction components present at nanomolar concentrations. Measurements are rapid and the image produced provides a permanent record. Luminescent assays, including immunoassays can be monitored on photographic film and there are no requirements of an external power source. An instrumental readout (reflectance or densitometer) may also be included if desired.

Thus, in accordance with the present invention, there is provided a luminescence detection device for quantitatively detecting an analyte in a liquid sample which comprises: (1) a compartment having, along a primary axis, opposite end portions, a first of which is for introduction of fluid reagents and sample into the compartment and the other of which forms a light transmissive aperature of predetermined size, said compartment being suitable to hold a composition which luminesces in response to contact with analyte-containing sample; (2) closure means in said first end portion for admitting a cannula, whereby fluid is introduced into said compartment, and for closing the compartment; (3) a photoresponsive imaging layer; (4) means for associating the photoresponsive imaging layer and the compartment such that the photoresponsive imaging layer is positioned, preferably substantially perpendicular to the primary axis of the compartment, at a predetermined distance from the end portion forming the aperture so as to be exposed to light emanating therefrom; and (5) means for preventing exposure of the photoresponsive imaging layer to ambient light.

Light emitted from the aperture exposes a zone of the imaging layer which it contacts. The amount of light emitted is proportional to the amount of analyte in the sample. Even at low analyte concentrations, the light exposes a "base zone" of the imaging layer. This "base zone" has the same area as the aperture. Increased analyte concentrations cause increased exposure of this "base zone" up to full exposure. The analyte concentration effective to fully expose the base zone can be selected by adjusting the concentration of reagents in the luminescent detection system. Analyte concentrations beyond this cause luminescence from the aperture to expose an area of greater diameter on the imaging layer. Thus, the exposed zone is of a size greater than the area of the base zone or aperture. Analyte concentrations in this range are proportional to the diameter of the exposed zone.

DESCRIPTION OF THE PREFERRED EMBODIMENTS

The reaction compartment can be comprised of one or more elements. For example, it can be a well in a preformed multiwell serial dilution or tissue culture plate, commonly molded of plastic. The luminescent reagents are placed directly in the well, the top of the plate covered and reagents and sample introduced into the well(s) through the cover. Alternatively, the reaction compartment can comprise a reaction vessel housing and a reaction vessel therein. The reaction vessel housing can for example, be an opaque block with cylindrical cavities bored vertically through it. The reaction vessel in this case can be a glass test tube which fits snugly into the cylindrical cavity.

In either embodiment, the compartment has a first end portion through which reagents and sample are introduced. This end is closed by closure means which can be penetrated by a cannula for introduction of fluid. The closure means can be integral with the reaction compartment or can be a separate element, such as a septum. As an example of the first embodiment, the reaction compartment can comprise a reaction vessel housing of rubber or other resilient material. The first end portion is closed over by a thin diaphragm of the resilient material which is formed as a portion of the overall block of material. Where the closure means is separated, it is preferably a septum or stopper such as has commonly been used with evacuated containers for the collection of blood samples.

The photoresponsive imaging layer is preferably photographic film. This can be black-and-white or color film. For convenience, it is preferably self-developing film.

Mechanical elements of the overall device provide structure sufficient to associate the photoresponsive imaging layer and the reaction compartment such that the photoresponsive imaging layer is positioned substantially perpendicular to the primary axis of the reaction compartment at a predetermined distance from the end portion forming the aperture so as to be exposed to light emanating therefrom. Such structure can be provided, for example, by a base having a horizontal chamber for accepting the photoresponsive imaging layer and, thereabove, a carriage for vertically holding the reaction compartment. The base can, optionally, further comprise a shutter assembly positioned between the reaction compartment and the photoresponsive imaging layer. Such a base serves, additionally, to block the photoresponsive imaging layer from exposure to ambient light. It is this embodiment which has been selected for illustration in FIGS. 1-4.

As shown in FIG. 1, the luminescence detection device, generally designated 10, comprises an opaque reaction vessel housing 12, a reaction vessel 14 and a photoresponsive imaging layer 16. The opaque reaction vessel housing 12, having a main body 20, is provided with a plurality of cylindrical side walls 22, each of which forms a vessel receiving chamber 24. Each vessel receiving chamber 24 is closed by means suitable to permit light tight introduction of syringe needle 26. The vessel receiving chamber 24 is also open at the bottom to form an aperture 18 of predetermined shape and size. The photoresponsive imaging layer 16 is positioned at a predetermined distance from the aperture 18 so as to be exposed to light emanating therefrom.

Figure 2:
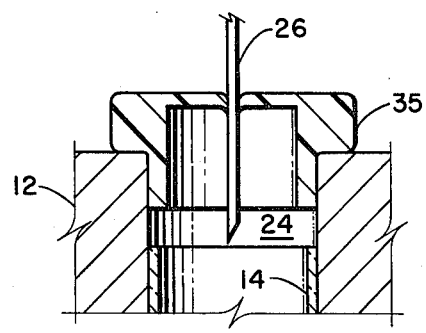
FIG. 2 is a partial, cross-sectional view of a similar preferred embodiment, emphasizing another form of closure.

The top of the vessel receiving chamber 24 can be enclosed by an integral closure 34 which is continuous with main body 20 thus forming a unitary element which is entirely opaque. Alternatively, as illustrated in FIG. 2, the top of the vessel receiving chamber 24 can be enclosed by a removable septum 35 which fits snugly into vessel receiving chamber 24 to form a removable light tight closure. In either embodiment, the closure of the vessel receiving chamber 24 is of a material having characteristics which allow it to be penetrated by a hypodermic needle 26 for introduction of fluids into reaction vessel 14 while remaining light tight. The reaction vessel housing 12 is intended to be made of any material suitable for forming a solid defined structure. Such can include opaque plastics, rubber, metal, or other known materials.

With continued reference to FIG. 1 reaction vessel 14 is positioned in reaction vessel housing 12. The reaction vessel 14 is formed of sidewalls 42 which fit coaxially with cylindrical sidewalls 22 of vessel housing 12 and a base portion 46 which is continuous with sidewalls 42. The base portion 46 can be either rounded or flat and is of such character as will not substantially effect a scattering of the light emanating from the reaction solution 48 which is held by reaction vessel 14. Reaction vessel 14 is limited at its upper end by opening 44. Thus, a needle inserted into vessel receiving chamber 24 can introduce fluid into reaction vessel 14 through opening 44. The reaction vessel 14 is intended to be made of any transparent or translucent material suitable for containing the intended luminescent reaction solution. Preferably such materials can include optically clear glass, quartz, plastic or other known materials. Conveniently, the reaction vessel 14 can be an optically clear test tube.

Figure 3:
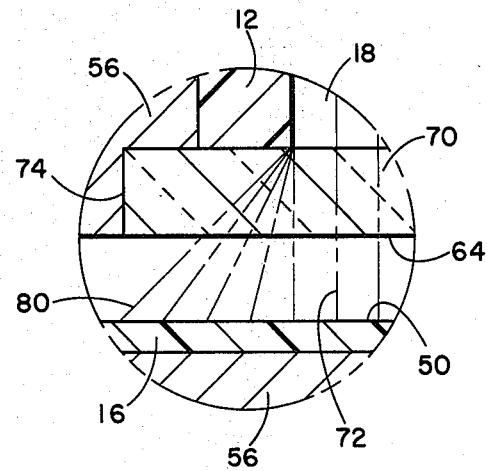
FIG. 3 is an enlarged view of the lower portion of FIG. 1, which is encircled by line 3.

With particular reference to the lower portion of FIG. 1 and the enlarged view provided by FIG. 3, the photoresponsive imaging layer 16 has a photosensitive surface 50 which faces aperature 18 so as to be exposed to light emanating therefrom. In laminar relation with photoresponsive imaging layer 16 is an opaque backing 56 which prevents exposure of photosensitive surface 50 by ambient light. Photoresponsive imaging layer 16 is held a predetermined distance from aperture 18 of reaction vessel housing 12 by suitable means, the illustrated embodiment of which is now described in more detail.

This embodiment of the invention includes a shutter 60 (FIG. 1 only) between the opaque reaction vessel housing 12 and the photoresponsive imaging layer 16. A shutter plate 62 (FIG. 1 only) slides (lateral motion depicted by arrow in FIG. 1) in shutter guide 64 and parallel to photoresponsive imaging layer 16. The shutter plate 62 is moved to the open position to allow light contact between the photosensitive surface 50 of imaging layer 16 and light emitting from aperature 18.

Additionally, there is provided a spacer 70 further enabling definition of the distance between aperture 18 and the photosensitive surface 50. The spacer 70 has an optically clear body 72 having spacer walls 74 of predetermined height for definition of distance. The optically clear body 72 of spacer 70 is preferably free of light scattering characteristics.

In another embodiment (not illustrated), a camera can be mounted on the opaque reaction vessel housing such that the aperture is in light exposure to the photoresponsive imaging layer, in this case photographic film, which is held in predetermined distance from the aperture 18 by a lens system, optionally including a shutter, which is suitable to provide the optically clear transmission of luminescence desired.

Figure 4:
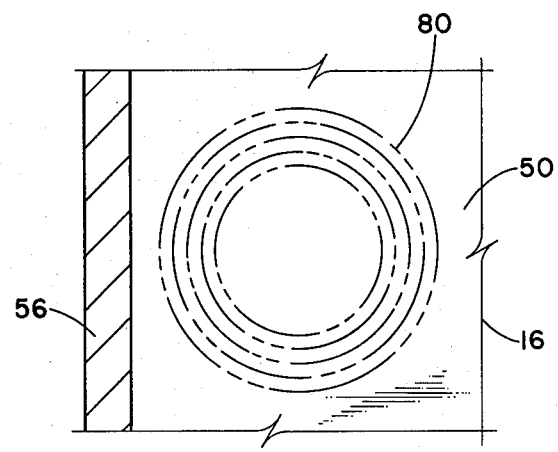
FIG. 4 is an enlarged representation of the concentric light exposures on the imaging layer of FIG. 1, taken along line 4—4.

FIG. 4 depicts, in phantom line, concentric rings 80 which outline increasing areas of light exposure on the photoresponsive surface 50 of the imaging layer 16. Also shown is a portion of the opaque backing 56. The device is used by a method of quantitatively detecting an analyte in a sample which comprises reacting the sample with a composition effective to produce light in response to the presence of said analyte in the reaction vessel and measuring the diameter of any exposure produced on the photoresponsive imaging layer thereof.

Figure 5:
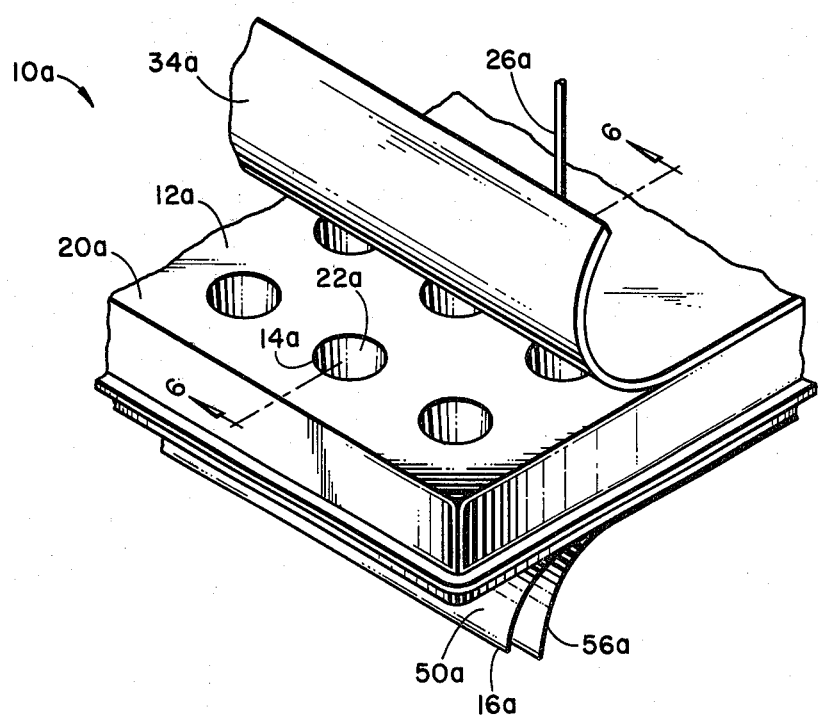
FIG. 5 is a exploded partial isometric view of another preferred embodiment of the luminescence detection device of the invention.
Figure 6:
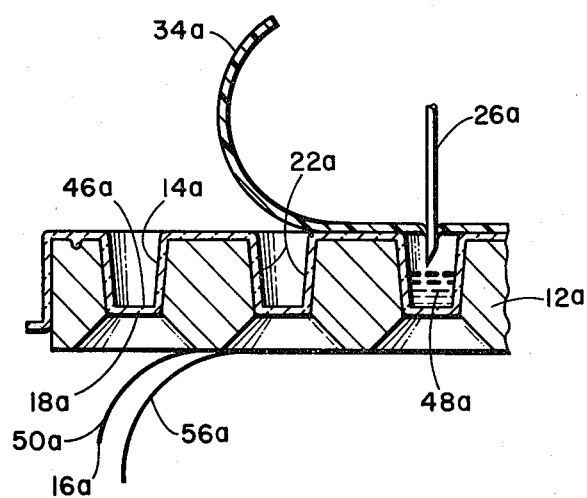
FIG. 6 is a cross-section view of the preferred embodiment of FIG. 5, taken along line 6—6.

Another preferred embodiment of the same invention is illustrated by FIGS. 5 and 6, wherein elements comparable to those in the embodiment illustrated by FIGS. 1-4 are assigned the same item numbers, but with the suffix "a".

As shown in FIGS. 5 and 6, the luminescence detection device, generally designated 10a, comprises an opaque reaction vessel housing 12a, a reaction vessel 14a and a photoresponsive imaging layer 16a. The opaque reaction vessel housing 12a, having a main body 20a, is provided with a plurality of cylindrical side walls 22a which, together with a base portion 46a which is continuous with side walls 22a, forms reaction vessel 14a. The base portion 46a must be transparent or translucent. Each vessel receiving chamber 24a is closed at the top by means suitable to permit light tight introduction of syringe needle 26a. Aperture 18a in this embodiment is provided by the base portion 46a. The photoresponsive imaging layer 16a is positioned at a predetermined distance from the aperture 18a so as to be exposed to light emanating therefrom.

The top of the reaction vessel 14a can be enclosed by an opaque, integral closure 34a which is continuous in covering main body 20a, thus forming a unitary seal, preferably fixed by adhesive. It may also have a light reflective inner surface laminated to it which increases light transmission to the film. Integral closure 34a is of a material having characteristics which allow it to be penetrated by a hypodermic needle 26a for introduction of fluids into reaction vessel 14a while remaining light tight. The reaction vessel housing 12a is intended to be made of any material suitable for forming a solid defined structure. Such can include opaque plastics, rubber, metal, or other known materials.

The photoresponsive imaging layer 16 has a photosensitive surface 50a which faces aperture 18a so as to be exposed to light emanating therefrom. In laminar relation with photoresponsive imaging layer 16a is an opaque backing 56a which prevents exposure of photosensitive surface 50a by ambient light. Photoresponsive imaging layer 16a is held in place a predetermined distance from aperture 18a by being fixed to the bottom of the reaction vessel housing 12a using, for example, a clamp or double-faced adhesive (not shown) on portions of photosensitive surface 50a which will not be exposed to light.

In a variation of this preferred embodiment it is possible to substitute a cartridge-like film pack which has a shutter mechanism for selectively exposing the imaging layer which is attached to the reaction vessel housing. The shutter can be opened just prior to initiation of the luminescent reaction by injection of the oxidant, e.g. hydrogen peroxide. The film pack, including the shutter, can then be removed and the film developed. In a variation of this embodiment a shutter can be provided which has holes of selected diameter positioned underneath each reaction vessel. Such a shutter with holes can act as a damper, i.e. smaller holes reduce the size of the base zone and increased diameter exposure area proportionately, thereby extending the measurements possible to high concentrations.

In either embodiment and whatever the variation of the elements of the device, certain types of luminescent reaction systems require wash steps in the preparation of the reagent configuration and others do not. For example, luminescent immunoassays generally require washing steps between the introduction of various reagents. As such a removable septum may be a more desirable variation under these circumstances than would a unitized assembly for the reaction vessel housing. Alternatively, assays for adenosine triphosphate (ATP) using luciferase can be added through an integral seal, as no washing step is needed.

LUMINESCENT SYSTEMS

Luminescence may be simply defined as the emission of visible or invisible radiation which is the result of a chemical reaction. In chemiluminescence the source of the energy that is producing molecules in an excited state is the energy of a chemical reaction, and the decay from the excited state back to the ground state is accompanied by emission of light (luminescence). Analytically, the types of luminescence that have engendered the most interest are chemiluminescence and bioluminescence. The latter is the name given to a special form of chemiluminescence found in biological systems, in which a catalytic protein increases the efficiency of the luminescent reaction.

1. Chemiluminescent Assay Systems

In summary, the mechanism of organic chemiluminescence in solution involves three stages: (a) preliminary reactions to provide the key intermediate, (b) an excitation step in which the chemical energy of the key intermediate is converted into excitation energy, and (c) emission of light from the excited product formed in the chemical reaction. In reactions in which a fluorescent compound is added to enhance the chemiluminescent emission, an efficient energy transfer occurs and the resulting chemiluminescence is known as "sensitized chemiluminescence".

Chemiluminescent reactions systems require an oxidant (usually hydrogen peroxide) which can be produced, as in step (a) above by preliminary reactions which produce the key intermediate. They also require a catalyst, for example microperoxidase, heme, hemoglobin or cobalt. Additionally they require a chemilumingenic compound which receives the excitation energy from the key intermediate (hydrogen peroxide) by the effect of the catalyst. When the chemilumingenic compound returns to its base state from the high energy excited state a release of energy is in the form of detectable light.

The chemiluminescent systems described in this section all have the common feature of being able to detect hydrogen peroxide, generally produced in preliminary reactions. The composition effective to produce light in response to an analyte is preferably of the type which comprises at least one enzyme responsive to the presence of the analyte in the sample to produce a reaction product, such as an oxidant like hydrogen peroxide. This enzyme is characteristically an oxidase, such as those known to be used in clinical analysis, such as glucose oxidase or cholesterol oxidase. Other known oxidants which are formed or used in other systems include periodate, hypochlorite, ferricyanide or permanganate. The hydrogen peroxide formed reacts with a peroxidatively active substance such as peroxidase.

The peroxidases are generally conjugated proteins containing iron porphyrin. Peroxidase occurs in horseradish, potatoes, figtree sap and turnips (plant peroxidase); in milk (lacto peroxidase); and in white blood corpuscles (verdo peroxidase); also it occurs in microorganisms and may be produced by fermentation. Certain synthetic peroxidases, such as those disclosed by Theorell and Maehly in Acta. Chem. Scand., Vol. 4, pages 422–434 (1950), are also satisfactory for use in $H_2O_2$ detection systems. Peroxidatively active substances are enzyme-like in that they catalyze the reduction of peroxides. Hemoglobin and its derivatives are typical of such "peroxidatively active" substances because they behave in a manner similar to the behavior of the enzyme peroxidase. Other substances which are not enzymes but which demonstrate peroxidative activity are: iron sulfocyanate, iron tannate, ferrous ferrocyanide, chromic salts (such as potassium chromic sulfate) absorbed in silica gel, etc.

Several different chemiluminescent systems are known in the art, and the following are examples, without limiting the scope of the present invention, of some such systems contemplated for use in the present detection system. The following systems are listed according to the nature of the chemiluminescent compound used.

(a) Diacylhydrazides

Strong chemiluminescence is obtained from cyclic diacyhydrazides having the formula:

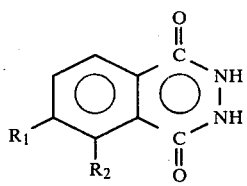

wherein one of $R_1$ and $R_2$ is hydrogen and the other is $-NR_3R_4$ wherein $R_3$ and $R_4$ are independently selected from hydrogen or a straight chain alkyl group containing 1-6 carbon atoms. One preferred compound is luminol (5-amino-2,3-dihydro-1,4-phthalazinedione) where $R_1$ is $-NH_2$ and $R_2$ is $-H$. Another preferred compound is isoluminol (6-amino-2,3-dihydrophthalazine-7,4-dione) where $R_1$ is $-H$ and $R_2$ is $-NH_2$. Substitution in the ring structure markedly influences, i.e. either increases or decreases, luminescence. A complete loss of light occurs if the heterocyclic ring is substituted. Schroeder, H. R. et al, Specific Protein Binding Reactions Monitored by Chemiluminescence, Immunoassays: Clinical Laboratory Techniques for the 1980's Alan R. Liss, Inc., New York, N.Y. 189–204 (1980).

Annealated analogs of luminol have been found which are even more efficient at light production than luminol. One example is a compound having the formula:

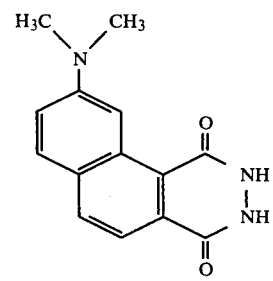

which is discussed in McCapra, F., The chemiluminescence of organic compounds. Q. Rev. (London) 20:485 (1966) and in Schroeder, H. R. and Yeager, F. M., Chemiluminescence Yields and Detection Limits of Isoluminol Derivatives in Various Oxidation Systems, Anal. Chem., 50:1114 (1978).

The efficiency, wavelength, and pH optimum of light emission in luminol depend greatly on reaction conditions. In general, hydrogen peroxide is the most commonly used oxidant; catalysts include $Fe(CN_6)^{3-}$ and $Cu^{2+}$, Seitz, W. R., and Neary, M. P., Chemiluminescence and Bioluminescence, Anal. Chem., 46:188 (1974). Other oxidants used include hypochlorite, iodine, permanganate, and oxygen in the presence of a suitable catalyst. Perhaps the most efficient catalyst in this reaction is heme, and the best medium a carbonate buffer. The optimum pH for chemiluminescence varies somewhat with the catalyst and oxidant, but that for most oxidizing systems is near pH 11. The luminescence of luminol follows the stoichiometry in Equation 1:

Equation 1

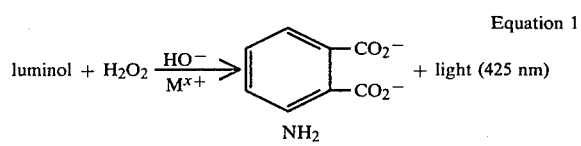

It has been shown that the aminophthalate ion, which is formed in the singlet excited state, is the light emitter in the reaction, White, E. H., and Bursey, M. M., Chemiluminescence of luminol and related hydrazides: The light emission step. J. Am. Chem. Soc. 86:941 (1964). The detection limit for luminol with the hydrogen peroxide/microperoxidase system is 1 picomol/liter.

(b) Acridinium Salts

Lucigenin (bis-N-methylacridinium nitrate) luminesces on oxidation by peroxide in basic solution in the presence of metal ion catalysts. The reaction is catalyzed by some metal ions, such as $Pb^{2+}$, that do not catalyze the luminol reaction and thus provides the basis for analytical applications not possible with luminol.

Acridinium phenyl carboxylates which undergo chemiluminescent oxidation with hydrogen peroxide are described in McCapra, F., Tutt, D., and Topping, R. M., The Chemiluminescence of Acridinium Phenyl Carboxylates in the Assay of Glucose and Hydrogen Peroxide. In Proceedings of the International Symposium on Analytical Applications of Bio- and Chemiluminescence, Brussels (1978) and in McCapra F. et al., U.K. Pat. No. 1,461,877 (1977). The optimum pH for oxidation of these substances depends on the nature of the substituent in the phenyl group, thus allowing an acridinium salt to be tailored to fit particular pH requirements.

(c) Diaryl Oxalates

Diaryl oxalates such as bis(trichlorophenyl) oxalate undergo a chemiluminescent oxidation reaction with hydrogen peroxide by way of a peroxyoxalate intermediate. See, for example, Sherman, P. A., Holtbecker, J., and Ryan, D. E., Analytical Applications of Peroxyoxalate Chemilunescence, Anal. Chim. Acta 97:21 (1978); Seitz, W. R., and Neary, M. P., Recent Advances in Bioluminescence and Chemiluminescence Assay. Methods Biochem. Anal. 23:161 (1976); and Williams, D. C., and Seitz, W. R., Automated Chemiluminescence Method for Determining the Reduced Form of Nicotinamide Adenine Dinucleotide Coupled to the Measurement of Lactate Dehydrogenase Activity, Anal. Chem. 48:1478 (1976).

Bis(trichlorophenyl) oxalate has been used, in a ethyl acetate/methanol/aqueous buffer (pH range 4-10) system containing triethylamine, for the analysis of peroxide. A fluorescent molecule, perylene, has been used as the light emitter in this reaction (sensitized chemiluminescence) because of its stability and its favorable efficiency and wavelength range of emission. Williams, D. C. Huff, G. G., and Seitz, W. R., Evaluation of Peroxylate Chemiluminescence for Determination of Enzyme Generated Peroxide, Anal. Chem. 48:1003 (1976). The detection limit is $7\times10^{-8}$ moles/liter (mol/L) and the linear response range extends up to $10^{-3}$ mol/L of hydrogen peroxide. Although the bis(trichlorophenyl) oxalate system is not as sensitive as luminol (see above) for the detection of peroxide it does have advantages of a lower background chemiluminescence and less sensitivity to interferants such as uric acid.

(d) Other Chemiluminescent Systems

Other chemiluminescent assay systems described in the art which can be used in the present invention include:

(i) lophine, which is oxidized in alkaline pH to give a yellow chemiluminescence (see Radzizewski, B., Untersuchung unber Hydrobenzamid, Ararin und Lophin Chem. Ber. 10:70 (1977);

(ii) siloxine, which is oxidized in acidic pH to give a yellow-red chemiluminescence (see Erdey, L., Chemiluminescence indicators In Indicators E. Bishop, Ed., Pergamon Press, Oxford, U.K. 1972, pp 709-732); and (iii) Polyhydric phenols such as pyrogallol and gallic acid (see Slawinska, D., and Slawinska, J., Chemiluminescent flow method for determination of formaldehyde Anal. Chem. 47:2101 (1975).

2. Bioluminescent Assay Systems

Numerous assays for substances of clinical interest are based on reactions involving cofactors such as nicotine adenine dinucleotide/reduced form ($NAD^+$/NADH) and adenosine triphosphate (ATP). The bioluminescent reactions described offer sensitive alternatives to the conventional spectrophotometric or colorimetric assays for such cofactors.

Although the firefly and glow-worm are the best-known bioluminescent organisms, most are sea-living organisms, ranging in complexity from microscopic bacteria and plankton to many species of fish. Several bioluminescent systems are known and the following are examples of some such systems contemplated for use in the present test device. They are first discussed according to the organisms which are the source of the bioluminescence and then summarized mechanistically.

(a) Firefly (Photinius)

Firefly luminescence undoubtedly has been the most extensively studied bioluminescent system. The light-producing reaction requires the enzyme luciferase, luciferin, $Mg^{2+}$, ATP, and molecular oxygen. Luciferase is a generic term referring to an enzyme that catalyzes the oxidation of a substrate, such as luciferin, with light emission. Luciferin is a generic term referring to a reduced compound that can be oxidized in an appropriate environment to produce an electronically excited singlet state; light is produced on its return to the ground state.

The initial reaction is the rapid conversion, in the presence of $Mg^{2+}$ and ATP, of luciferin to luciferyl adenylate, which, in the presence of luciferase, combines with molecular oxygen to give an oxyluciferyl adenylate-enzyme complex in the excited state. After emission, the ground-state complex disassociates to form enzyme, adenosine monophosphate (AMP), oxyluciferin, and carbon dioxide, the last being derived from the carboxyl group of luciferin. The reaction is best carried out at 25° C. in glycine buffer at pH 7.8. The color of the light emitted differs for different species of firefly, although the structure of luciferin is identical for all species. Intensity and wavelength of maximal emission are also altered by changes in pH, ionic strength, temperature, and the presence of chlorides of $Zn^{2+}$ or $Cd^{2+}$.

The reaction is not specific for ATP; other nucleotides such as cytidine-5'-triphosphate, inosine-5'-triphosphate, and iso-ATP can stimulate light emission. Manganese cations may replace $Mg^{2+}$ in the reaction. Certain anions inhibit the reaction ($SCN-<I-<NO^3-<Br-<Cl-$). Anesthetics such as procaine and lidocaine are also inhibitors, and this fact has formed the basis of assays.

(b) Marine Bacteria

Most studies of luminescent marine bacteria have centered on two types *Beneckea Harveyi* (*Photobacterium fischeri* strain MAV) and *Vibrio Fischeri*. In vitro, the components required for luminescence are reduced flavin mononucleotide $FMNH_2$ generated from FMN by the oxidation of NADH or NADPH with the aid of FMN reductase, a long-chain aliphatic aldehyde (R—CHO), oxygen, and bacterial luciferase. The total light produced in the reaction is proportional to the amount of each of the substrates ($O_2$-$FMNH_2$, and R—CHO) when they are present in limiting quantities. This is also true of the luciferase because excess $FMNH_2$ is auto-oxidized so rapidly as compared with the rate of light emission that $FMNH_2$ has been reconverted to FMN by the time the luciferase finishes its catalytic cycle. Thus, like the other reactants, the luciferase only acts once in the in vitro reaction. It is however, capable of turnover on repeated addition of $FMNH_2$. The aldehyde is oxidized to the corresponding carboxylic acid. Only aliphatic aldehydes (R—CHO) with a chain length (R) of eight or more carbon atoms are effective in the reaction.

Microbial luciferase activity is highly specific for $FMNH_2$, but the enzyme also shows weak activity towards other flavins and flavin analogs. Luciferase is particularly sensitive to thiol reagents such as p-chloromercuribenzoic acid and to reagents that react with lysyl, cysteine and histidinyl residues. Volatile anesthetics, riboflavin, and cyanide, and copper, iron, and other heavy metals also inhibit the enzyme.

Flavin mononucleotide reductase (flavin reductase, NAD(P)H dehydrogenase, or NAD(P)H-FMN oxidoreductase) appears to associate in vitro with bacterial luciferase. FMN reductases isolated from *Vibrio fischeri* and *Beneckea harveyi* both show appreciable activity in NADH oxidation over a relatively broad pH range, from about pH 5 to pH 10. Riboflavin, FAD, and isomers and analogs of FMN may act as substrates for FMN reductase.

(c) Jellyfish (Aequorea)

The bioluminescent system of the jellyfish Aequorea consists of protein-chromophore complexes (termed "photoproteins"), which react with $Ca^{2+}$ to produce a bluish luminescence, maximum wavelength is 469 nanaometers (nm), independent of dissolved oxygen. The photoprotein consists of a species-specific protein in close association with a chromophore component (luciferin), which is oxidized by the protein in the presence of $Ca^{2+}$ to oxyluciferin, with production of light. The spent photoprotein is termed "blue-fluorescent protein". Metal ions other than $Ca^{2+}$ which can catalyze the *Aequorea system* are $Sr^{2+}$, $Ba^{2+}$, and all of the lanthanides.

(d) Reaction Mechanisms

In summary, those bioluminescent systems which are suitable for use in clinical chemistry systems can be schematically represented as follows:

(i) Pyridine-nucleotide linked

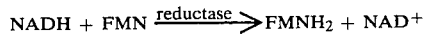

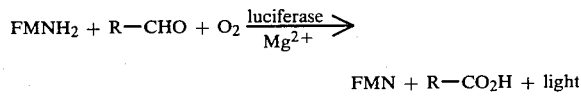

(ii) Adenine-nucleotide linked

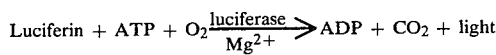

(iii) Enzyme-substrate systems

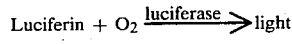

(iv) Activation of "precharged" systems

3. Luminescent Immunoassays

The development of specific binding assay techniques has provided useful analytical methods for determining various organic substances of diagnostic, medical, environmental and industrial importance which appear in liquid mediums at very low concentrations. Specific binding assays are based on the specific interaction between the ligand, i.e, the bindable analyte under determination, and a binding partner therefor. Where one of the ligand and its binding partner is an antibody and the other is a corresponding hapten or antigen, the assay is known as an immunoassay.

In conventional specific binding assay techniques, a sample of the liquid medium to be assayed is combined with various reagent compositions. Such compositions include a label conjugate comprising a binding component incorporated with a label, in this case a luminescent label. The binding component in the label conjugate participates with other constituents, if any, of the reagent composition and with the ligand in the medium under assay. This forms a binding reaction system in which two species, a bound-species and a free-species, the binding component is not so bound. The relative amount or proportion of the label conjugate that results in the bound-species compared to the free-species is a function of the presence (or amount) of the ligand to be detected in the test sample.

Where the label conjugate in the bound-species is essentially indistinguishable in the presence of the label conjugate in the free-species by the means used to monitor the label, the bound-species and the free-species must be physically separated in order to complete the assay. This type of assay is referred to in the art as "heterogeneous". Where the bound-species and free-species forms of the label conjugate can be distinguished in the presence of each other, the separation step can be avoided, and the assay is said to be "homogeneous".

The luminescent immunoassays which are described here are exemplary of those which are applicable to analytical chemistry.

(a) Luminescent Immunoassays

Immunoassays which use luminescent labels (L) such as luminol, isoluminol, luciferase, or luminol derivatives have been reported. A general schematic (Antigen- = Ag; Antibody = Ab) is as follows:

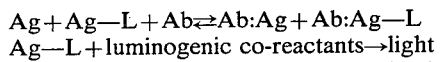

Compared with radioimmunoassay, luminescent immunoassay (LIA) has many of the advantages associated with enzyme immunoassay, i.e. (1) the reagents are cheap and stable, (2) assays are rapid and can be automated, (3) a separation step may not be required (homogeneous), radiation hazards are obviated, and, in addition, these method offer the added advantage of very sensitive detection of the label (Wisdom, G. B., Enzyme-immunoassay Clin. Chem. 22:1243 (1976) review).

Heterogeneous and homogeneous luminescent immunoassays have been described. The luminescent activity of a luminol-IgG conjugate reportedly is unaffected when bound to an antibody (Hersch, L. S., et al., A Luminol-Assisted Competitive-Binding Immunoassay of Human Immunoglobulin G, Anal. Biochem. 93:267 (1979). In contrast, the luminescent activity of an isoluminol-biotin conjugate increases 10-fold when bound to avidin, a binding protein specific for biotin. This enhancement in light output has been ascribed to increased chemiluminescent efficiency mediated by the protein [see Schroeder, H. R., Vogelhut, P. O., Carrico, R. J., et al., Competitive Protein Binding Assay for Biotin Monitored by Chemiluminescence, Anal. Chem.

48:1933 (1976)]. Also, a heterogeneous competitive binding immunoassay for thyroxine (T4) monitored by chemiluminescence has been described which uses a thyroxine label conjugate. Schroeder, H. R., et al., Immunoassay for Serum Thyroxine Monitored by Chemiluminescence, J. Immunol. Methods 25:275 (1979).

(b) Luminescent Enzyme Immunoassay

Luminescent assays for enzymes, such as peroxidase (POD) are considerably more sensitive than are conventional colorimetric assays, a factor that has been exploited in the quantitation of enzyme conjugates in enzyme immunoassays. A luminescent enzyme immunoassay for cortisol involving luminescent quantitation of a peroxidase-cortisol conjugate has a sensitivity comparable with that of the radioimmunoassay [see Arakawa, H., Maeda, M., and Tsuji, A., Enzyme Immunoassay of Cortisol by Chemiluminescence Reaction of Luminol—Peroxidase. Bunseki Kagaku 26:322 (1977)]

A schematic (antigen=Ag; Antibody=Ab) of this type of assay is as follows:

Ag+Ag—POD+Ab⇌Ab:Ag+Ab:Ag—POD
Ag—POD+luminogenic co-reactants→light (c) Luminescent Cofactor Immunoassay Several workers have recently investigated enzymic methods for monitoring specific binding reactions, using ligand-cofactor (cofactor=CF) conjugates quantitated by use of a bioluminescent reaction: Carrico, J. R., Yeung, K. K., Schroeder, H. R. et al, Specific Protein-binding Reactions Monitored With Ligand-ATP Conjugates and Firefly Luciferase, Anal. Biochem. 72:95 (1976); Carrico, R. J., Christner, J. E., Boguslaski, R. C., and Yeung, K. K., A Method for Monitoring Specific Binding Reactions With Cofactor Labeled Ligands, Anal. Biochem 72:271 (1976); and Schroeder, H. R., Carrico, R. J. Boguslaski, R. C., and Christner, J. E., Specific Binding Reactions Monitored With Ligand-cofactor Conjugates and Bacterial Luciferase Anal. Biochem 72:283 (1976).

The ligand has, for example, been covalently coupled to an enzymically active derivative of NAD+. After reduction with alcohol dehydrogenase and ethanol, these conjugates can be measured quantitatively by means of light production by using the bacterial luciferase system. The light production of ligand-NADH can be inhibited by a protein that specifically binds to the ligand; thus specific binding reactions can be assayed without separating free and bound labeled ligands (homogeneous). As ATP can be measured in very low concentrations with firefly luciferase, the possibility of labeling ligands with this cofactor has also been investigated by these workers. A schematic (antigen=Ag; Antibody=Ab) of this type of assay is as follows:

Ag+Ag—CF+Ab⇌Ab:Ag+Ab:Ag—CF
Ag—CF+luminogenic co-reactions→light (d) Luminescent Enzyme-Multiplied Immunoassay It has also been suggested to monitor drugs using the enzyme-multiplied immunoassay technique by using the NADH-dependent bacterial luminescence system, because in many cases the enzyme label (E) used is an oxidoreductase, such as a dehydrogenase. (see Stanley P. E., Application of Analytical Bioluminescence to the Enzyme Multiplied Immunoassay Technique, In Liquid Scintillation Counting 5, P. Johnson and M. Crook, Eds., Heyden and Son, London 1978, p. 79).

4. Luminescent Enzyme Assays

An assay for amidase activity of α-chymotrypsin has been developed using Boc- and Z-alanylalanyl-phenylalanamido-4-aminophthalhydrazide. The synthetic substrates release isoluminol when hydrolyzed by the enzyme. Isoluminol production is determined by measuring its chemiluminescence. Kinetic constants of the luminescent substrates were measured with α-chymotrypsin, and levels of the enzyme as low as 50 ng were determined. A comparison of similar luminescent, chromogenic, and fluorescent substrates is presented. Hranchini B. R., et al., Sensitive Enzyme Assays Based on the Production of Chemiluminescent Leaving Groups, Anal. Biochem. 111:87 (1981).

The following examples illustrate preferred embodiments of the invention.

EXAMPLE I

A method of achieving a sensitive, rapid photographic measurement of chemiluminescence is illustrated using the device according to the invention. Since the detection limit of chemiluminescent labels on photographic film had previously been unknown, this was investigated for ultimately monitoring immunoreactions in highly sensitive oxidation systems.

Device Construction

A Polaroid camera (Graphic Polaroid Back Graflex, Inc., Rochester, N.Y.) was adapted to monitor chemiluminescence. Briefly, the lens fixture was removed and a sliding metal plate was attached as a shutter. Above this was positioned a thin clear plastic plate and an aluminum block with an array of twelve 6.5 millimeter (mm) diameter holes which accommodated 6 mm×50 mm glass reaction tubes. A lid of aluminum served to keep out room light. Holes countersunk in the lid above each tube held rubber septa which were kept in place by a plastic plate with 1 mm holes to serve as needle guides. The camera was loaded with blue sensitive Polaroid Pola Scope film, Type 410, 8.3×10.8 cm with speed of 10000 ASA.

Experimental Procedure

Reaction compositions containing 2.5 micromolar (μM) microperoxidase and varying levels of 7-[N-(4-aminobutyl)-N-ethyl]-aminonaphthalene-1,2-dicarboxylic acid hydrazide (ABENH) in 50 milliMolar (mM) NaOH were dispensed as 140 μl aliquots into the reaction tubes which were then placed in the individual light-tight wells above the film. The shutter was then opened. A 20 μl aliquot of hydrogen peroxide in 10 mM Tris hydroxymethyl aminomethane hydrochloride (Tris-HCl), at pH 7.5, was hand injected from a gas-tight 50 μl syringe into each tube to initiate light production. The shutter was closed two (2) minutes or more after the last injection, which was sufficient for all reactions to cease light production. Thus, the film measured the integral of chemiluminescence.

Results

After development, the picture showed white spots on a black background at a position opposite to the position in the reaction holder (end-over photographic inversion). The photosensitive surface produced an exposed portion having defined exposure diameters in response to luminescent reaction of the reaction solution and light emitted therefrom. Spots first increased in intensity from a black background through gray to white and then in size, with increasing concentration of ABENH.

Table 1 summarizes the data obtained:

TABLE I

DETECTION OF ABENH ON POLAROID FILM

| ABENH (nM) | Spot Size (mm) | Spot Appearance |
|---|---|---|
| 0.00 | — | black |
| 0.47 | — | black |
| 0.94 | — | very faint gray |
| 1.41 | — | light gray |
| 1.88 | 4 | gray |
| 2.81 | 5 | white |
| 3.75 | 9 | white intense |
| 4.69 | 10 | white intense |
| 5.63 | 11.5 | white intense |
| 7.50 | 13 | white intense |
| 9.38 | 15 | white intense |
| 11.25 | 16.5 | white intense |

Figure 7:
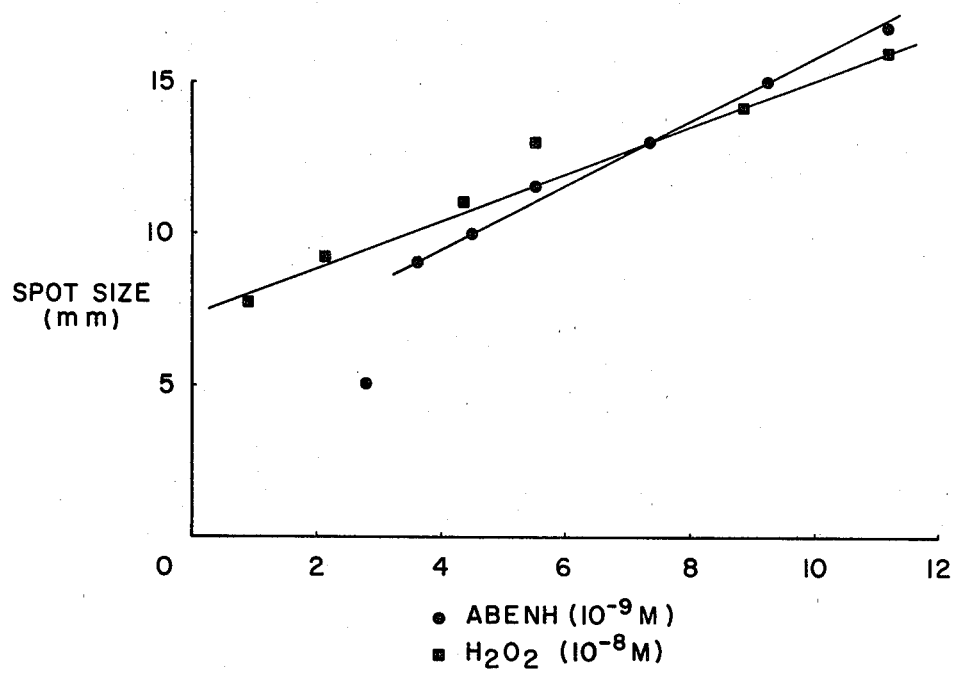
FIG. 7 is a graphical representation of the data reported in Example I.

The sharp contrast of white on black background allowed sensitive visual determination. Once the film area beneath the light producing reaction was maximally exposed, a linear increase in spot size was observed with increased concentration of ABENH. FIG. 7 is a graphical representation of the data reported in Table 1.

The light from the reaction behaves essentially as a point source about 5 mm above the film. The confining opaque cylindrical cavity produces the observed umbrella effect in spot enlargement. This novel feature allowed easy visual quantitation of analytes.

EXAMPLE II

In the experiments reported by this example a chemiluminescent reagent system was exposed to a range of hydrogen peroxide ($H_2O_2$) concentrations to evaluate its ability to provide a quantitative response using the device of the invention. A broad spectrum of enzymatic systems are known which produce $H_2O_2$ in response to a variety of clinically significant analytes. As such, this example encompasses a comparison which is not limited to any particular analyte.

Device Construction

The experiments of this example were performed using the device constructed as described in Example I.

Experimental Procedure

Aliquots of a solution containing 2.5 $\mu$M ABENH and 2.5 $\mu$M microperoxidase in 50 mM NaOH (pH 13) were dispensed into clean test tubes of the device. The device was then sealed for injection of the reaction initiating reagent, $H_2O_2$. The shutter was opened and aliquots (20 $\mu$l) of 10 mM tris-HCl containing various $H_2O_2$ concentrations were then injected into the test tubes. As before the shutter was closed only after the emission of light had ceased.

Results

On development pictures showed a white spot on black background. Once it reached maximum exposure, this spot increased in size with concentration of analyte. Concentrations indicated in Table 2 are those in the final 160 $\mu$l of the reaction:

TABLE 2

DETECTION OF $H_2O_2$ ON POLAROID FILM

| $H_2O_2$ (nm) | Spot Size (mm) | Spot Appearance |
|---|---|---|
| 0 | 5 | light gray |
| 5.6 | 5 | gray |
| 11 | 7 | gray white |
| 23 | 9 | white intense |
| 45 | 11 | white intense |
| 46 | 13 | white intense |
| 90 | 14 | white intense |
| 113 | 16 | white intense |

The resultant data show that devices, prepared according to the invention, provide quantitatively detectable signals which are responsive to the concentration ranges of the hydrogen peroxide present.

Although the invention has been described with particularity, numerous changes in the details can be resorted to without departing from the scope of the invention.

What is claimed is:

1. A luminescence detection device for quantiatively detecting an analyte in a liquid sample, which device comprises
   (1) an opaque reaction compartment having, along a primary axis, opposite end portions, a first of which is for introduction of fluid reagents and sample into the compartment and the other of which forms a light transmission aperture of predetermined size, the compartment being suitable to hold a composition which luminesces in response to contact with analyte-containing sample;
   (2) closure means in said first end portion for admitting a cannula, whereby fluid is introduced into said compartment, and for closing the reaction compartment;
   (3) a photoresponsive imaging layer;
   (4) means for associating the photoresponsive imaging layer and the reaction compartment such that the photoresponsive imaging layer is positioned at a predetermined distance from the end portion forming the aperture so as to be exposed to light emanating therefrom; and
   (5) means for blocking the photoresponsive imaging layer from exposure to ambient light.

2. The device of claim 1 wherein the reaction compartment comprises an opaque reaction vessel housing and a reaction vessel therein.

3. The device of claim 2 wherein the reaction vessel is transparent.

4. The device of claim 1 wherein the closure means is an integral portion of the compartment.

5. The device of claim 1 wherein the closure means is a septum.

6. The device of claim 1 wherein the photoresponsive imaging layer is photographic film.

7. The device of claim 1 wherein the photoresponsive imaging layer is self-developing photographic film.

8. The device of claim 1 wherein the means for associating the photoresponsive imaging layer and reaction compartment comprises a base having a horizontal chamber for accepting the photoresponsive imaging layer and, thereabove, a carriage for vertically holding the reaction compartment.

9. The device of claim 8 wherein the base further comprises a shutter assembly positioned between the reaction compartment and the photoresponsive imaging layer.

10. The device of claim 8 wherein the base blocks the photoresponsive imaging layer from exposure to ambient light.

* * * * *